(12) United States Patent
Lercher et al.

(10) Patent No.: US 7,459,412 B2
(45) Date of Patent: Dec. 2, 2008

(54) CATALYST FOR ACID-CATALYZED BY HYDROCARBON CONVERSIONS

(75) Inventors: Johannes A. Lercher, Ottobrunn (DE); Andreas Feller, München (DE); Stefan Gaab, Burgberg im Allgäu (DE)

(73) Assignee: Sud-Chemie AG, Munich (DE)

( * ) Notice: Subject to any disclaimer, the term of this patent is extended or adjusted under 35 U.S.C. 154(b) by 636 days.

(21) Appl. No.: 10/478,446

(22) PCT Filed: Feb. 20, 2002

(86) PCT No.: PCT/EP02/01822

§ 371 (c)(1),
(2), (4) Date: Apr. 28, 2004

(87) PCT Pub. No.: WO02/094436

PCT Pub. Date: Nov. 28, 2002

(65) Prior Publication Data

US 2004/0181108 A1 Sep. 16, 2004

(30) Foreign Application Priority Data

May 22, 2001 (DE) ................................. 101 24 998

(51) Int. Cl.
*B01J 29/06* (2006.01)
(52) U.S. Cl. .............................. 502/60; 502/73; 502/74; 502/77; 502/79
(58) Field of Classification Search ................... 502/60, 502/73, 74, 77, 79
See application file for complete search history.

(56) References Cited

U.S. PATENT DOCUMENTS

| 3,251,902 A | 5/1966 | Garwood |
| 3,591,488 A | 7/1971 | Eberly |
| 3,647,916 A | 3/1972 | Caesar |
| 3,803,256 A | 4/1974 | Kirsch |
| 3,839,228 A | 10/1974 | Kirsch |
| 3,840,613 A | 10/1974 | Eberly, Jr. |
| 3,865,894 A | 2/1975 | Kirsch |
| 3,867,307 A | 2/1975 | Scherzer |
| 3,893,942 A | 7/1975 | Yang |
| 4,125,591 A | 11/1978 | Lindsey |
| 4,300,015 A | 11/1981 | Kirsch et al. |
| 4,377,721 A | 3/1983 | Chester |
| 5,073,665 A | 12/1991 | Child |

FOREIGN PATENT DOCUMENTS

| DE | 19745548 | 4/1999 |
| WO | WO 97/20787 | 6/1997 |
| WO | WO 97/45383 | 12/1997 |

OTHER PUBLICATIONS

Haas, A., "FCC catalysts containing the high-silica faujasites EMO and EMT for gas-oil cracking." *Microporous and Mesoporous Materials* 28 (1999) 325-333.

Occelli, M.L. "The effects of Na. ions on the properties of calcined rare earth Y (CREY) zeolites." *Applied Catalysis A: General* 183 (1999) 53-59.

Borade, R.B. "Characterization of Acid Sites in Beta and ZSM-20 Zeolites." *Journal of Physical Chemistry*. 1992, 96, 6729-6737.

Notice of Opposition to European Patent No. EP 1 395 361 B1 (patent application No. 02719887.8) filed by Albemarle Corporation against Sud-Chemie AG dated Apr. 11, 2007.

*Primary Examiner*—Elizabeth D Wood
(74) *Attorney, Agent, or Firm*—Scott R. Cox

(57) ABSTRACT

A catalyst for acid-catalyzed hydrocarbon conversions, in particular for the alkylation of olefins with isoparaffins, containing a crystalline zeolite with an $SiO_2$—$Al_2O_3$ molar ratio of <10, the alkali cations of which are at least partially replaced by $H^+$ ions and/or polyvalent cations, the residual concentration of alkali cations amounting to less than around 0.2% by weight, the concentration of the Bronsted centers, determined as a function of the pyridine chemisorbed on the catalyst surface, amounting to around 0.1 to 4 mmol/g of catalyst, and the ratio between the concentration of the acid centers of the Bronsted type (B) and of the Lewis type (L), expressed as the surface ratio of the absorption bands at 1540 ±5 $cm^{-1}$ (B) and 1450 5 $cm^{-1}$ (L) after heating to a temperature of 450° C amounting to around 1.4 or higher, is described.

13 Claims, 3 Drawing Sheets

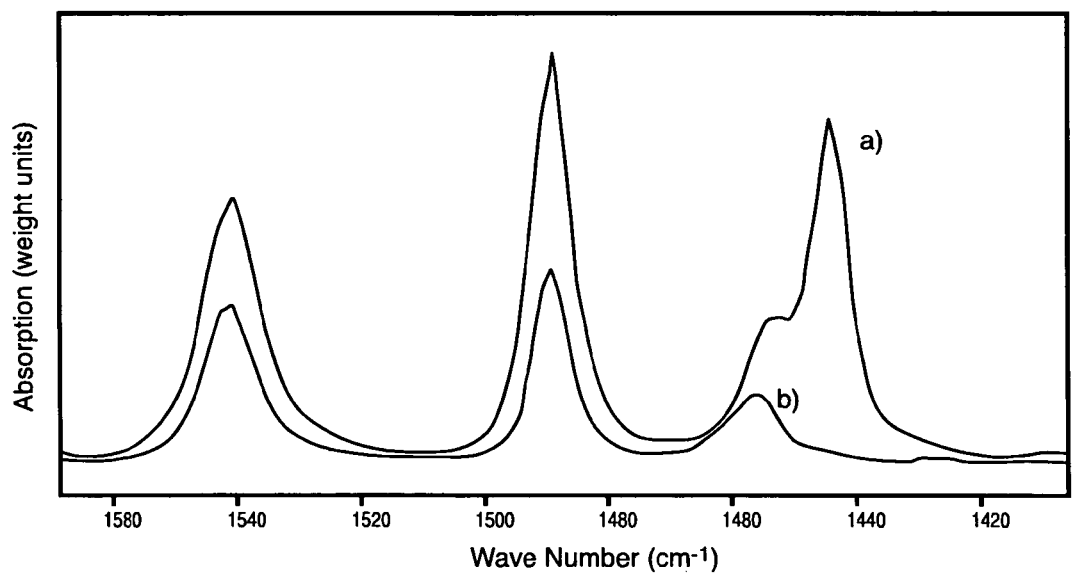
Fig. 1: IR spectra of pyridine absorbed on the catalyst from Example 1, at a temperature of a) 100°C and b) after desorbing at 450°C, measured after cooling to 100°C.

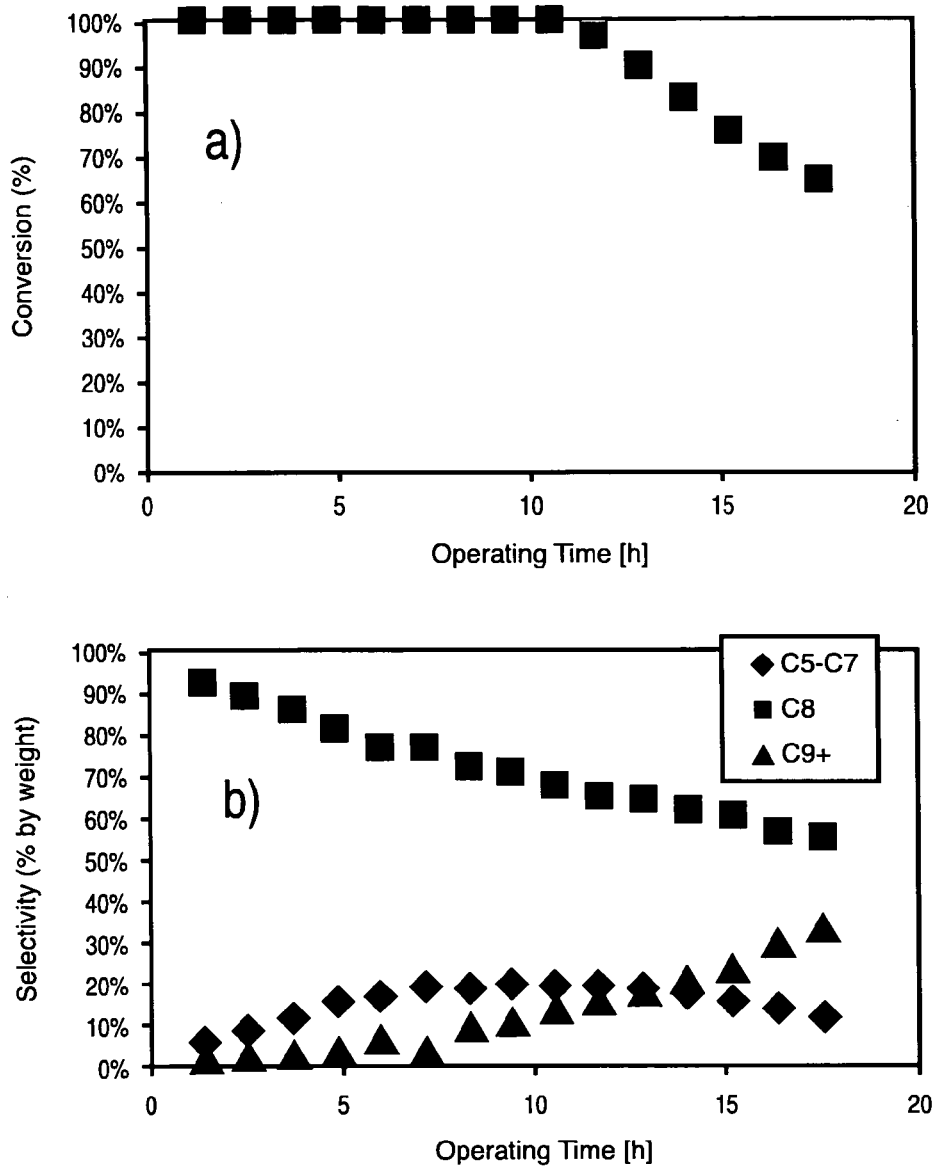
Fig. 2: Butane conversion (a) and product selectivities (b) over the operating time measured with the catalyst in accordance with Application Example 1.

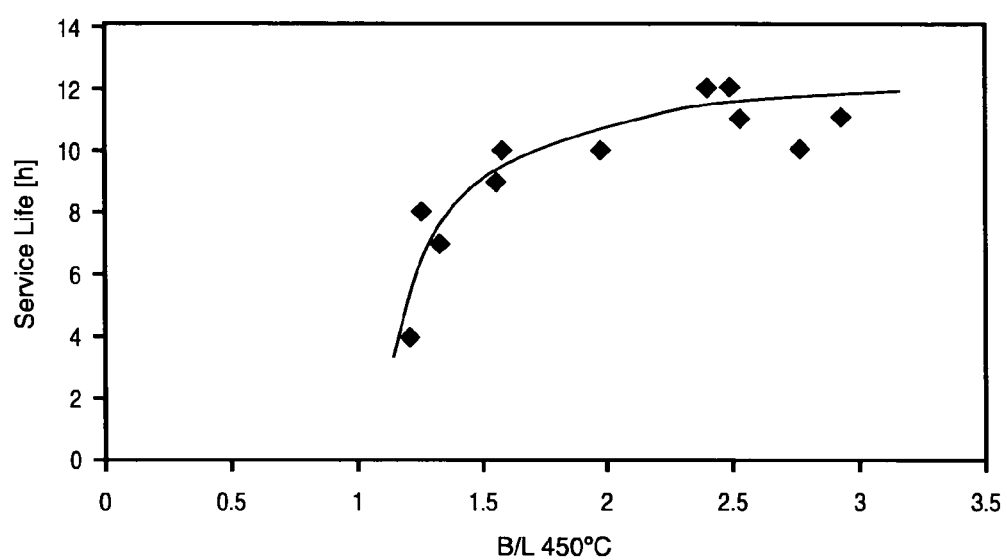
Fig. 3: Connection between Bronsted/Lewis acid center ration and the service life of the catalysts from Example 4.

CATALYST FOR ACID-CATALYZED BY HYDROCARBON CONVERSIONS

The invention concerns a catalyst for acid-catalyzed hydrocarbon conversions, in particular for the alkylation of olefins with isoparaffins, containing a crystalline zeolite with an $SiO_2$—$Al_2O_2$ molar ratio of <10, the alkali cations of which are at least partially replaced by $H^+$-ions and/or polyvalent cations. Zeolite catalysts of this kind are known in the art.

Thus, DE-B 197 45 548 describes a catalyst for the alkylation of $C_2$ to $C_5$ olefins with isoparaffins for producing a high-octane-containing additive for fuels.

The catalyst consists of a highly porous, ion-exchanged crystalline aluminum silicate (e.g. a Y or X zeolite), to which a metal of group VIII of the periodic system (e.g. Pd or Pd/Ni) is applied in an amount of 0.02 to 0.50% by weight and has the following chemical composition:

$Re_aM_bNa_c((Al_1Si_x)-O_2) \cdot yH_2O$

RE being an element chosen from the group of lanthanum and the lanthanides except from Cer, and M being an alkaline earth metal, such as Ca, and:

a=0.10 to 0.30; b=0.05 to 0.25; c=0.01 to 0.05; x=1.0 to 3.0; y=3.0 to 5.0.

The catalyst has a very low concentration of acid centers of the Bronsted type because of its relatively high alkaline earth metal content.

U.S. Pat. No. 3,676,368 (DE-A-2 142 270) describes an alkali faujasite with an $SiO_2$—$Al_2O_3$ molar ratio of more than 3, which contains 6 to 14% by weight of rare earth ions (as oxides), and which was produced according to the following method:

a) Replacement of an alkali faujasite with an $SiO_2$—$Al_2O_3$ ratio of around 3 to 6 with a solution of rare earth ions with a pH value of 3.0 to 3.5, in order to reduce the alkali content to less than 4% by weight;

b) Calcining the exchanged faujasite at a temperature of around 427 to 760° C. over 1 to 3 hours, and c) Replacing the calcined faujasite with a solution of ammonium ions, in order to reduce the alkali content to less than 0.5% by weight.

The sequence of the replacement of the alkali metal by the rare earths and the replacement with ammonium ions is important in this method.

According to a further development described in U.S. Pat. No. 3,867,307, the faujasite is replaced with a mixture of 10 to 13% by weight of rare earth ions and 0.5 to 5% by weight of a transition metal from the group of zinc, cadmium, potassium, zirconium, manganese, cobalt, nickel, and copper. Most of these metals form weaker Bronsted centers. The modified faujasite contains less than 3% by weight alkali.

U.S. Pat. No. 4,377,721 describes a method for alkylating isoparaffins with olefins in the presence of a catalyst in the form of a synthetic crystalline zeolite of the ZSM-20 type. The catalyst has an unfavorable ratio of acid centers of the Bronsted type to the Lewis type.

U.S. Pat. No. 5,073,665 describes a method for alkylation of olefins with isoparaffins with the use of a catalyst in the form of an unpromoted synthetic zeolite MCM-22. The catalyst was steam-treated, which leads to a de-alumination of the crystal lattice.

A similar method concerns WO 97/20787, a faujasite, active centers of which are up to 30% replaced by rare earth cations, being used. This catalyst was preliminarily de-aluminized.

WO 97/45383 concerns a method for alkylation of olefins with isoparaffins with the use of a zeolite having large pores and a particle size in the range of 20 to 200 µm. Faujasite and zeolites X and Y may be used as catalysts. The zeolites contain cations of rare earth metals and not more than 1.0% by weight sodium. No more detailed data about the catalyst were given. The selectivity for the desired isooctane fraction is low, that is, a high portion of cracking products is obtained, which greatly increases the vapor pressure of the fuel.

U.S. Pat. Nos. 3,839,228, 4,300,015, 3,865,894, and 3,803,256 concern methods for the alkylation of olefins with isoparaffins with the use of acid zeolites, that also may contain rare earth ions. The catalysts have an unfavorable ratio between the acid centers of Bronsted and Lewis type.

U.S. Pat. No. 3,251,902 concerns a method for alkylating branched-chain hydrocarbons with the use of a crystalline aluminum silicate catalyst having pore openings of at least 7 Å. The catalyst may be a rare earth metal containing faujasite. In addition, it may contain $H^+$ ions. The catalyst has an unfavorable ratio between acid centers of the Bronsted and Lewis type.

U.S. Pat. No. 3,647,916 concerns a method for alkylating branched chain hydrocarbons by causing a $C_4$ to $C_{20}$ isoparaffin with a $C_2$ to $C_{12}$ olefin with the use of a crystalline aluminosilicate catalyst, e.g. a rare earth or faujasite containing $H^+$ ions. The catalyst also contains a relatively high portion of sodium ions.

The object of the invention is to produce a catalyst for acid-catalyzed hydrocarbon conversions, in particular for alkylating olefins with isoparaffins, on the basis of crystalline zeolites, which catalyst has an excellent selectivity. In particular, on the one hand the formation of cracking products, and on the other hand the formation of polymeric deposits on and in the pores of the catalyst is minimized and the service life of the catalyst is maximized.

Thus, the object of the invention is a catalyst for acid-catalyzed hydrocarbon conversions, in particular for the alkylation of olefins with isoparaffins, containing a crystalline zeolite having an $SiO_2$—$Al_2O_3$ molar ratio of <10, the alkali cations of which are replaced at least partially by $H^+$ ions and/or tri- or polyvalent cations, the residual concentration of alkali cations amounting to less than around 0.2% by weight, the concentration of the Bronsted centers, determined as a function of the pyridine chemisorbed on the catalyst surface, amounting to around 0.1 to 4 mmol/g of catalyst, and the ratio between the concentration of the acid centers of the Bronsted type (B) and of the Lewis type (L), expressed as the surface ratio of the absorption bands at 1540±5 cm$^{-1}$ (B) and 1450±5 cm$^{-1}$ (L) after heating to a temperature of 450° C. amounting to 1.4 or higher.

Surprisingly, for such zeolytic alkylating catalysts it was found that they have the highest possible concentration of Bronsted acid centers of a specific strength and a low concentration of strong Lewis acid centers. The latter centers usually arise from aluminum cations, that during the modification process are released from the crystal lattice, in particular during the calcining step. The greater the scale of this process, the lower the concentration of the Bronsted acid centers becomes, and the higher that of the Lewis acid centers becomes. Lewis acid centers are catalytically inactive, but bind olefins, whereby the oligomerization is accelerated. The carbenium ions bonded to the Bronsted acid centers desorb as alkanes with the aid of isobutane, via the hydride transfer step.

On the one hand, a high concentration of Bronsted acid centers leads to high activity of the catalyst, since a large number of carbenium ions are present in the reaction volume.

On the other hand, surprisingly, it was observed that the stability of the carbenium ions becomes lower with increasing concentration of aluminum and their release by hydride transfer from isobutane is clearly increased. This leads to a suppression of cleavage reactions and oligomerization and causes a higher service life as well as selectivity of the catalyst.

The determination of the adsorbed amount of pyridine and the Bronsted/Lewis acid center ratio takes place in an infrared spectrometer. First, the catalyst sample is pressed into a tablet without a binder, and put into a measuring cell, that then is evacuated. The sample is activated for around 1 hour at 450° C. Then pyridine is introduced at a temperature of around 100° C. as gas with a pressure of around $10^{-2}$ mbar. Saturation is achieved when hydroxyl bands at 3640±10 and 3600±10 $cm^{-1}$ have disappeared. Then the sample is evacuated at $10^{-6}$ mbar, in order to remove more weakly bonded pyridine. After temperature-programmed heating of the sample to 450° C., the surface ratio of the absorption band of the pyridine is measured at 1540±5 $cm^{-1}$ (B) and 1450±5 $cm^{-1}$ (L).

Preferred embodiments are cited in the subclaims.

Preferably the portion of the pyridine not yet desorbed from the Bronsted acid centers at a temperature of 450° C. amounts to around 10 to 80%, in particular around 30 to 60%, of the pyridine bonded to Bronsted centers at 100° C.

Preferably the ratio between the concentration of the centers of the Bronsted type (B) and the Lewis type (L) amounts to around 1.5 to 6, in particular around 1.5 to 5.

The $SiO_2$—$Al_2O_3$ molar ratio is preferably <7, in particular around 2 to 6.

The polyvalent cations are preferably cations of the rare earth metals.

The $H^+$ form of the zeolite preferably is obtained by replacing the alkali cations with $NH_4^+$ ions and subsequent calcination.

Preferably, the zeolite is built out of 12- to 18-member rings of $SiO_2$ and $AlO_2$ units, and has an effective pore size of around 0.6 to 2 nm. Preferably it is a faujasite of type X, Y, or LSX, or a zeolite of the EMT or ZSM-20 type.

The concentration of the Bronsted acid centers preferably amounts to around 0.2 to 4, in particular around 0.5 to 2 mmol/g of catalyst.

The catalyst may additionally contain at least one metal of the $8^{th}$ transition element group, in particular a metal of the platinum group, in an amount of around 0.01 to 0.05% by weight.

By means of the addition of a metal of the $8^{th}$ transition element group the catalyst may be regenerated more easily, whereby its overall service life is increased. The addition of noble metals, such as platinum, is known from U.S. Pat. No. 3,893,942. It is indicated there that a partially deactivated zeolitic catalyst, which is exchanged with platinum, can be regenerated by treatment with hydrogen. In the case of the regeneration of the catalysts, the polymeric products resting in the pores are split under hydrogenating conditions, and removed from the catalytic material. The metals of the $8^{th}$ transition group have no influence on the alkylation.

In principle, the regeneration also may be performed by treating the catalyst loaded with the polymers with oxygen or an oxygen-containing gas. However, this reaction is strongly exothermic, therefore it is less preferred.

Further, the object of the invention is the use of the catalyst in accordance with the invention for acid-catalyzed hydrocarbon conversions, in particular for the alkylation of olefins with isoparaffins, for example of $C_2$-$C_6$ olefins with $C_4$-$C_6$ isoparaffins. The conversion is carried out at temperatures of around 0 to 200° C., in particular from around 50 to 120° C., preferably from around 60 to 100° C., and particularly preferably in the liquid phase, at least one of the educts being liquid at the reaction temperature. For this purpose the conversion preferably is carried out at around 4 to 40 bar.

However, a reaction in the gas phase also is conceivable.

The invention is explained in a non-limiting way by the following examples.

EXAMPLE 1

50 g of a commercial zeolite X having an $SiO_2/Al_2O_3$ molar ratio of 2.6 and a sodium content of 14% by weight were suspended in 300 ml of a 0.2 molar lanthanum nitrate solution and heated while stirring at 80° C. for 2 hours. The solution was filtered off, and the filter cake was treated again with 300 ml of 0.2 molar lanthanum nitrate solution without washing. The filter cake obtained after filtration and washing had a sodium content of 2% by weight. The filter cake was dried over night at 100° C., then ground and calcined in a tube oven in an air flow, the temperature being heated from 120° C. to 200° C. over a time period of 8 hours, whereupon it was heated to 450° C. at 3° C./min. This temperature was held constant for 1 more hour.

Then the calcined product was subjected to 4 more lanthanum exchange steps, as described above. The filter cake obtained after the washing and filtering was calcined as indicated above. The product had a sodium content of 0.05% by weight.

The sample obtained was investigated by IR spectroscopy as described above. The ratio of Bronsted to Lewis acid centers measured after heating to 450° C. amounted to 2.9. The IR spectrum at 100° C. and after heating to 450° C. is shown in FIG. 1. After heating to 450° C. the portion of the Bronsted-bonded pyridine amounted to 55% of the total amount of pyridine bonded at 100° C.

EXAMPLE 2

The procedure of Example 1 was repeated, with the difference that the sample also was additionally treated with 400 ml of a 0.05 molar ammonium nitrate solution at 80° C. for 2 hours before the second calcining. The filter cake obtained after washing and filtering was calcined as indicated in Example 1. During the calcining the amount of ammonium was desorbed, which corresponds to an $H^+$ concentration of around 0.01 mmol/g of catalyst. The total concentration of acid Bronsted centers was determined as being 0.57 nmol/g. The catalyst had a residual sodium content of 0.04% by weight. The ratio of Bronsted to Lewis acid centers measured after the heating to 450° C. amounted to 2.4. The portion of the Bronsted-bonded pyridine at 450° C. amounted to 37% of the pyridine bonded at 100° C.

EXAMPLE 3

The procedure of Example 1 was repeated; with the difference that the product was triturated with 500 ml of distilled water before the last calcining step and a solution with 0.2 g of tetraamino palladium(II) chloride was added while stirring over a period of 4 hours. After a further 24 hours the sample was washed and filtered. The filter cake was calcined in an air flow as described above, and then treated in a hydrogen flow at 300° C. for 4 hours, the noble metal being reduced. The noble metal content of the sample amounted to around 0.2% by weight after the calcining.

EXAMPLE 4

The procedure of Example 1 was repeated on a series of samples, the sequence of the exchange, the concentrations of the exchange solutions, and the intermediate calcination being varied. The preparation steps, the sodium content, and the B/L ratio at 450° C. are presented in Table 1.

TABLE 1

| sample | modification procedure | Na-content (% by weight) | B/L 450° C. |
|---|---|---|---|
| 1 | 1st stage: La-exchange; 2nd stage: $NH_4$ exchange | 0.09 | 1.3 |
| 2 | 1st stage: La-exchange; 2nd stage: $NH_4$ + La exchange | 0.002 | 2.0 |
| 3 | 1st stage: La-exchange; 2nd stage: La exchange | 0.004 | 2.5 |
| 4 | 1st stage: La-exchange; 2nd stage: $NH_4$ + La exchange | 0.002 | 1.2 |
| 5 | 1st stage: $NH_4$ + La exchange; no 2nd stage | 0.19 | 1.3 |
| 6 | 1st stage: La-exchange; 2nd stage: $NH_4$ + La exchange | 0.03 | 1.6 |
| 7 | 1st stage: La-exchange; 2nd stage: $NH_4$ + La exchange | 0.10 | 1.6 |
| 8 | 1st stage: La-exchange; 2nd stage: $NH_4$ + La exchange | 0.05 | 2.5 |
| 9 | 1st stage: La-exchange; 2nd stage: $NH_4$ + La exchange | 0.04 | 2.8 |
| 10 | Example 1 | 0.05 | 2.9 |
| 11 | Example 2 | 0.04 | 2.4 |

APPLICATION EXAMPLE 1

4 to 5 g of the catalyst of Example 1 were introduced into a 50 ml stirring boiler reactor and activated with nitrogen at 180° C. over night. After cooling to the reaction temperature of 75° C. the reaction vessel was filled with isobutane under a pressure of 32 bar. The isobutane was liquid under these conditions. After driving the stirrer at 1800 rpm a mixture of isobutane and 2-butene in a molar ratio of 6.7:1 was conducted through the reaction vessel. The space velocity, with respect to butene, amounted to 0.2 g butene per gram of catalyst and hour.

The product mixture was drawn off via the top and separated from the catalyst by a particle filter. The pressure of the product flow was released via a pressure regulator and the product flow was conducted through lines heated to around 150 to 180° C. through a 6-way valve, which fed a sample for analysis into a gas chromatograph for analysis every 70 minutes. Based on the chromatogram selectivity and conversion rates of the reaction were calculated. As shown in FIG. 2, the butene conversion amounted to 100% over a time period of 11 hours, which dropped to around 60% after 6 more hours. The selectivity, with respect to the total product amounted to 92% by weight isooctane, 5% by weight $C_5$ to $C_7$ paraffins and 3% by weight $C_{9+}$ paraffins at the beginning.

After 11 hours the selectivities, referred to the total product, were as follows: 69 wt % isooctane, 17 wt % $C_5$ to $C_7$ paraffins, 14 wt % $C_{9+}$ paraffins. Olefinic hydrocarbons were not detected.

APPLICATION EXAMPLE 2

The catalyst in accordance with Example 2 was investigated for the catalytic activity and selectivity under the same conditions as according to Application Example 1. The butane conversion amounted to 100% over a time period of 12 hours and then dropped. The selectivity with respect to the total product amounted to 93% by weight isooctane, 5% by weight $C_5$ to $C_7$ paraffins and 2% by weight $C_{9+}$ paraffins at the beginning. After 12 hours the selectivities, with respect to the total product, were as follows: 68% isooctane, 18% by weight $C_5$ to $C_7$ paraffins and 14% by weight $C_{9+}$ paraffins.

APPLICATION EXAMPLE 3

The palladium-containing catalyst in accordance with Example 3 was also tested under the same conditions as in accordance with Application Example 1. Here also the butene conversion amounted to 100% after 11 hours. The selectivity with respect to the total product amounted to 92% by weight isooctane, 5% by weight $C_5$ to $C_7$ paraffins and 3% by weight $C_{9+}$ paraffins at the beginning. After 11 hours the selectivities, with respect to the total product, were as follows: 69% isooctane, 17% by weight $C_5$ to $C_7$ paraffins and 14% by weight $C_{9+}$ paraffins.

APPLICATION EXAMPLE 4

The catalysts of Example 4 were all tested under the same conditions as in Application Example 1. The samples displayed different service lives, defined as the period of 100% butene conversion, from 4 to 12 hours. FIG. 3 shows how the service life of the catalyst depends on the Bronsted/Lewis acid center ratio measured at 450° C. The service life rises with the B/L ratio up to a value of 1.5 and then remains largely constant.

The invention claimed is:

1. A catalyst for acid-catalyzed hydrocarbon conversions, in particular for the alkylation of olefins with isoparaffins, comprising a crystalline faujasite of the X, Y or LSX type with an $SiO_2$-$Al_2O_3$ molar ratio of <10, wherein alkali cations are at least partially replaced with trivalent or polyvalent cations, wherein the residual concentration of alkali cations is less than about 0.2% by weight, wherein the concentration of Bronsted acid sites, determined as a function of pyridine chemisorbed on the catalyst surface, comprises about 0.1 to 4 mmol/g of catalyst, and wherein the ratio between the concentration of the acid sites of the Bronsted type (B) and of Lewis type (L), expressed as a surface ratio of absorption bands at $1540 \pm 5$ cm$^{-1}$ (B) and $1450 \pm 5$ cm$^{-1}$ (L) after heating to a temperature of 450° C is about 1.4 or higher, wherein the portion of the pyridine not yet desorbed from the catalyst surface at a temperature of 450° C which is bonded to the Bronsted acid sites comprises about 30 to 60 wt % of the pyridine chemisorbed at the Bronsted acid sites at 100° C.

2. The catalyst of claim 1, wherein the ratio between the concentration of the acid sites of the Bronsted type (B) and of the Lewis type (L) is about 1.5 to 6.

3. The catalyst of claim 1, wherein the $SiO^2$-$Al_2O_3$ molar ratio is less than about 7.

4. The catalyst of claim 1, wherein the polyvalent cations are cations of rare earth metals.

5. The catalyst of claim 1, wherein the through pore openings of the zeolite are comprised of 12- to 18-member rings.

6. The catalyst of claim 1, wherein the zeolite has an effective pore size of about 0.6 to 2 nm.

7. The catalyst of claim 1, wherein the concentration of the acid sites is about 0.2 to 4 mmol/g of catalyst.

8. The catalyst of claim 1 further comprising at least one metal of the $8^{th}$ transition element group, in an amount of about 0.01 to 0.5% by weight.

9. The catalyst of claim 1 further comprising at least one metal of the platinum group in an amount from about 0.01 to 0.5% by weight.

10. The catalyst of claim 1 wherein the $SiO_2$–$Al_2O_3$ molar ratio is from about 2 to 6.

11. The catalyst of claim 1, wherein the concentration of the acid sites is about 0.5 to 2 mmol/g of catalyst.

12. The catalyst of claim 1 wherein the ratio between the concentration of the acid sites of the Bronsted type (B) and of the Lewis type (L) is about 1.5 to 5.

13. The catalyst of claim 1, wherein the alkali cations of the crystalline faujasite are replaced at least partly with $H^+$ ions.

* * * * *